US00PP12143P2

(12) United States Plant Patent
Danziger

(10) Patent No.: US PP12,143 P2
(45) Date of Patent: Oct. 16, 2001

(54) NEW GUINEA IMPATIENS PLANT NAMED 'DANHARDKRD'

(75) Inventor: Gabriel Danziger, Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 09/323,096

(22) Filed: Jun. 1, 1999

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—Wendy Couchoud Baker
(74) *Attorney, Agent, or Firm*—Foley & Lardner

(57) ABSTRACT

A new and distinct cultivar of Impatiens plant named 'Danhardkrd' characterized by having large, round, dark-red flowers borne above the foliage, dark green foliage, and compact growth habit.

1 Drawing Sheet

BACKGROUND OF THE INVENTION

The present invention comprises a new and distinct cultivar of New Guinea Impatiens plant, botanically known as Impatiens, and hereinafter referred to by the cultivar name 'Danhardkrd'.

'Dankardkrd' is a product of a planned breeding program and was originated from a hybridization made by the inventor, Gabriel Danziger, in a controlled breeding program in Mishmar Hashiva, Israel, in 1996. The female parent was an Impatiens cultivar designated D-153. The male parent was an Impatiens cutlivar designated E-166. Both parents are proprietary cultivars used in the breeding program.

'Danhardkrd' was discovered and selected as a flowering plant within the progeny of the stated cross by the inventor, Gabriel Danziger, in 1997 in a controlled environment in Mishmar Hashiva, Israel.

The first act of asexual reproduction of 'Danhardkrd' was accomplished when vegetative cuttings were taken from the initial selection in 1997 in a controlled environment in Mishmar Hashiva, Israel by Gabriel Danziger. The cuttings are apical cuttings, cut from mother plants in the greenhouse. Horticultural examination of plants grown from these cuttings in Mishmar Hashiva, Israel, has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristics of 'Danhardkrd' which in combination distinguish this Impatiens as a new and distinct cultivar:

1. Large, round, dark-red flowers borne above the foliage;
2. Dark green foliage; and
3. Compact growth habit.

'Danhardkrd' has not been observed under all possible environmental conditions. The phenotype of the new cultivar may vary significantly with variations in environment such as temperature, light intensity, and daylength without any change in the genotype of the plant. The following observations, measurements and values describe the new cultivar as grown in Mishmar Hashiva, Israel under greenhouse conditions which closely approximate those generally used in commercial practice.

BRIEF DESCRIPTION OF THE DRAWING

The accompanying color photographic drawing shows typical flower and foliage characteristics of 'Danhardkrd', with colors being as true as possible with illustrations of this type.

DETAILED BOTANICAL DESCRIPTION

The measurements were taken in Mishmar Hashiva, Israel, and are based on plants grown from rooted cuttings in a net-covered greenhouse during the spring at temperatures of 30° C. maximum and 18° C. minimum. In the following description, color references are made to The Royal Horticultural Society Colour Chart (R.H.S), except where general colors of ordinary significance are used.

Species: *Impatiens hawkeri.*

Classification:

*Botanical.*—A hybrid of the genus Impatiens.

*Commercial.*—New Guinea Impatiens, cv. 'Danhardkrd'.

Plant:

*General appearance and form.*—Height: 15–20 cm. Width: 25–30 cm. Habit: Compact, rounded. Branching: Vigorous in character. Flowering response: 8–9 weeks after planting of rooted cuttings. Flowering season: Throughout the entire year; the plant is an annual plant. It grows in partially shaded areas in temperatures of 10C.–25C. degrees. Lasting quality of bloom: Open during the lifetime of the plant; bloom lastingness ranges between 5–10 days after anthesis. Propagation: Leaf-cutting. Rooting: Vigorous, roots initiate in 6–7 days at 25° C. and 8–9 days at 20° C.

Stem: 184 A, length 20 cm, diameter 0.8 cm, internode length 6 cm.

Spur: 47C.

Fragrance: Flowers have no fragrance.

*Foliage.*—Shape of leaf: Lanceolate. Base: Acuminate. Tip: Attentuate. Margin: Serrated ciliated. Texture: Smooth without pubescence. Length of leaf: 8.5–9.5 cm. Width of leaf: 2.5–3 cm. Main color on upper surface: Mature leaf: RHS 131 A. Immature leaf: RHS 137 A. Main color on lower surface: Mature leaf: RHS 199 B. Immature leaf: RHS 197 B. Veination: Upper surface: One main, red vein RHS 53B. Lower surface: One main, red vein RHS 53B and red veinations along the main vein.

Inflorescence:

*Corolla.*—Form: 5 petals per flower. Shape: Round. Average number: 20–25. Size: 5.5–6 cm. Petal number: 5. Petal shape: 4 are heart-shaped. The dorsal petal is free. The lateral petals are fused in pairs, the dorsal petal is wider than the lateral petals and is also heart-shaped. Petal color: Upper surface: In spring when opening, petals are red, RHS 45 B, without fading. Lower surface: RHS 42 B.

*Pedicel color.*—RHS 144D.

*Bud.*—Response: 6–7 weeks after planting of rooted cuttings, developing into open flowers approximately two weeks later. Size before opening: 2–2.5 cm. Aspect: Stands above pedicel and has a spur 4 cm long. Pedicle length: 3.5–4 cm. Bud color: 43A.

*Reproductive organs.*—Stamens: 1. Anthers: Round, light-red in color. Pollen: White. Stigma: Round, nearly white in color. Style: Green. Ovary: Four-celled, 1 mm in length, red in color. Seeds: Smooth, 1 mm in width, 2–3 mm in length, elliptic shape.

Disease resistance: This variety is not distinctively resistant or susceptible to plant disease.

Fruit/seeds: No fruit observed. Seeds are smooth, 1 mm in width, 2–3 mm in length, elliptic in shape.

I claim:

1. A new and distinct cultivar of Impatiens plant named 'Danhardkrd', as illustrated and described herein.

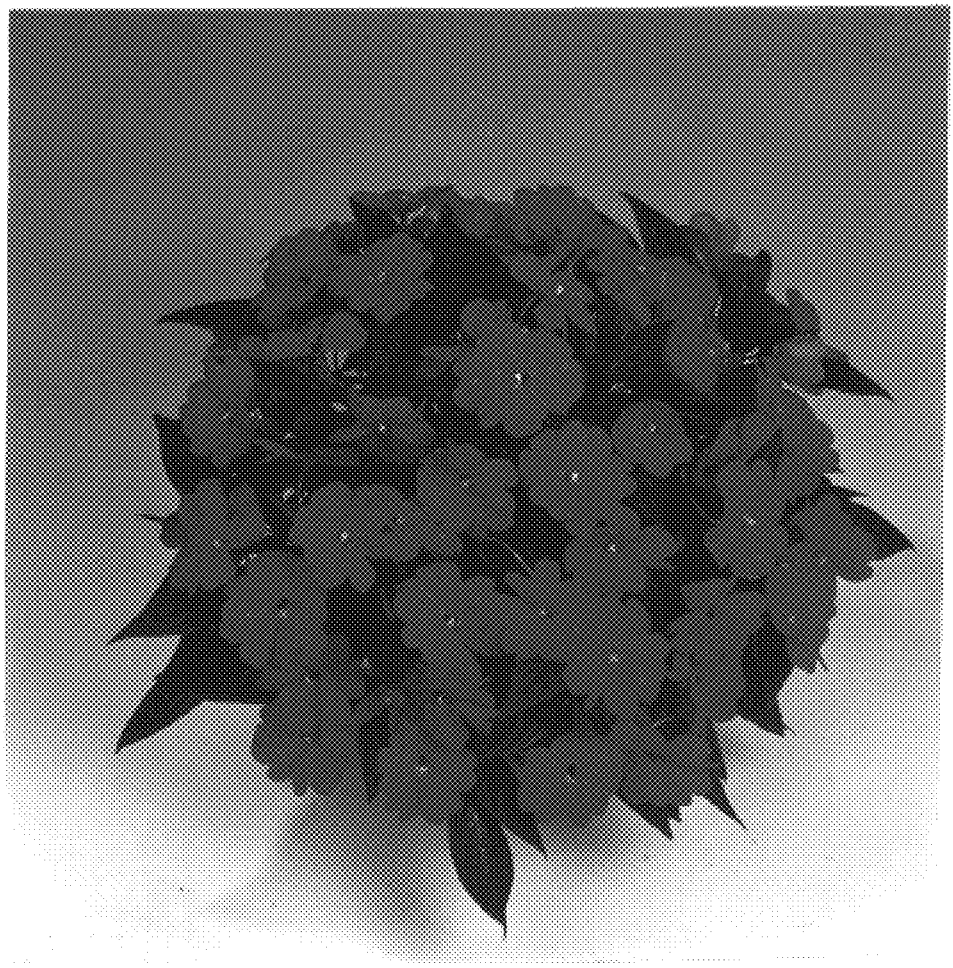

* * * * *